(12) United States Patent  (10) Patent No.: US 8,216,316 B2
Kirschman  (45) Date of Patent: Jul. 10, 2012

(54) PROSTHETIC IMPLANT WITH BIPLANAR ANGULATION AND COMPOUND ANGLES

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 523 days.

(21) Appl. No.: 12/336,753

(22) Filed: Dec. 17, 2008

(65) Prior Publication Data

US 2010/0152853 A1 Jun. 17, 2010

(51) Int. Cl.
*A61F 2/44* (2006.01)
(52) U.S. Cl. ...................... 623/17.16; 606/99
(58) Field of Classification Search .... 623/17.11–17.16; 606/99
See application file for complete search history.

(56) References Cited

U.S. PATENT DOCUMENTS

| | | |
|---|---|---|
| 2,677,369 A | 5/1954 | Knowles |
| 3,228,393 A | 1/1966 | Michele |
| 3,426,364 A | 2/1969 | Lumb |
| 3,848,601 A | 11/1974 | Ma et al. |
| 3,867,728 A | 2/1975 | Stubstad et al. |
| D245,259 S | 8/1977 | Shen |
| 4,309,777 A | 1/1982 | Patil |
| 4,349,921 A | 9/1982 | Kuntz |
| 4,501,269 A | 2/1985 | Bagby |
| 4,714,469 A | 12/1987 | Kenna |
| 4,743,256 A | 5/1988 | Brantigan |
| 4,759,769 A | 7/1988 | Hedman et al. |
| 4,820,305 A | 4/1989 | Harms |
| 4,834,757 A | 5/1989 | Brantigan |
| 4,863,477 A | 9/1989 | Monson |
| 4,878,915 A | 11/1989 | Brantigan |
| 4,904,261 A | 2/1990 | Dove et al. |
| 4,932,969 A | 6/1990 | Frey et al. |
| 4,946,378 A | 8/1990 | Hirayama et al. |
| 4,955,908 A | 9/1990 | Frey |
| 4,961,740 A | 10/1990 | Ray |
| 4,963,152 A | 10/1990 | Hofmann |
| 5,015,247 A | 5/1991 | Michelson |
| 5,062,850 A | 11/1991 | MacMillan |
| 5,071,437 A | 12/1991 | Steffee |
| 5,108,438 A | 4/1992 | Stone |
| 5,122,130 A | 6/1992 | Keller |
| 5,123,926 A | 6/1992 | Pisharodi |
| 5,147,402 A | 9/1992 | Bohler |
| 5,171,278 A | 12/1992 | Pisharodi |
| 5,171,281 A | 12/1992 | Parsons et al. |
| 5,192,327 A | 3/1993 | Brantigan |
| 5,258,031 A | 11/1993 | Salib |
| 5,282,861 A | 2/1994 | Kaplan |
| 5,306,308 A | 4/1994 | Gross et al. |
| 5,306,309 A | 4/1994 | Wagner et al. |
| 5,320,644 A | 6/1994 | Baumgartner |
| 5,344,459 A | 9/1994 | Swartz |
| 5,360,430 A | 11/1994 | Lin |
| 5,370,697 A | 12/1994 | Baumgartner |
| 5,397,364 A | 3/1995 | Kozak |
| 5,425,772 A | 6/1995 | Brantigan |
| 5,443,514 A | 8/1995 | Steffee |
| 5,458,638 A | 10/1995 | Kuslich et al. |
| 5,458,642 A | 10/1995 | Beer |

(Continued)

*Primary Examiner* — Eduardo C Robert
*Assistant Examiner* — Ellen C Hammond
(74) *Attorney, Agent, or Firm* — Jacox, Meckstroth & Jenkins

(57) ABSTRACT

A prosthetic implant, and more particularly, with a prosthetic implant having biplanar angulation and that can be inserted into a disk area generally straight using a posterolateral approach.

36 Claims, 13 Drawing Sheets

U.S. PATENT DOCUMENTS

| | | |
|---|---|---|
| 5,458,643 A | 10/1995 | Oka et al. |
| 5,514,180 A | 5/1996 | Heggeness |
| 5,534,028 A | 7/1996 | Bao |
| 5,534,030 A | 7/1996 | Navarro et al. |
| 5,545,229 A | 8/1996 | Parsons et al. |
| 5,554,191 A | 9/1996 | Lahille |
| 5,593,409 A | 1/1997 | Michelson |
| 5,609,637 A | 3/1997 | Biedermann et al. |
| 5,658,337 A | 8/1997 | Kohrs et al. |
| 5,676,702 A | 10/1997 | Ratron |
| 5,702,449 A | 12/1997 | McKay |
| 5,702,450 A | 12/1997 | Bisserie |
| 5,716,415 A | 2/1998 | Steffee |
| 5,728,159 A | 3/1998 | Stroever et al. |
| 5,755,798 A | 5/1998 | Papavero et al. |
| 5,766,252 A | 6/1998 | Henry et al. |
| 5,776,199 A | 7/1998 | Michelson |
| 5,824,094 A | 10/1998 | Serhan et al. |
| 5,861,041 A | 1/1999 | Tienboon |
| 5,865,845 A | 2/1999 | Thalgott |
| 5,888,226 A | 3/1999 | Rogozinski |
| 5,888,227 A | 3/1999 | Cottle |
| 5,897,556 A | 4/1999 | Drewry et al. |
| 5,989,289 A | 11/1999 | Coates et al. |
| 6,022,376 A | 2/2000 | Assell et al. |
| 6,045,580 A | 4/2000 | Scarborough et al. |
| 6,059,829 A | 5/2000 | Schlapfer et al. |
| 6,080,158 A | 6/2000 | Lin |
| 6,093,205 A | 7/2000 | McLeod et al. |
| 6,132,465 A | 10/2000 | Ray et al. |
| 6,139,579 A | 10/2000 | Steffee et al. |
| 6,143,031 A | 11/2000 | Knothe et al. |
| 6,146,422 A | 11/2000 | Lawson |
| 6,156,067 A | 12/2000 | Bryan et al. |
| 6,159,244 A | 12/2000 | Suddaby |
| 6,235,059 B1 | 5/2001 | Benezech et al. |
| 6,245,108 B1 | 6/2001 | Biscup |
| 6,277,149 B1 | 8/2001 | Boyle et al. |
| 6,302,914 B1 | 10/2001 | Michelson |
| 6,315,797 B1 | 11/2001 | Middleton |
| 6,387,130 B1 | 5/2002 | Stone et al. |
| 6,402,785 B1 | 6/2002 | Zdeblick et al. |
| 6,579,318 B2 | 6/2003 | Varga et al. |
| 2005/0107880 A1* | 5/2005 | Shimp et al. ............... 623/17.11 |
| 2006/0217806 A1* | 9/2006 | Peterman et al. .......... 623/17.11 |
| 2008/0154375 A1* | 6/2008 | Serhan et al. ............. 623/17.16 |
| 2009/0198339 A1* | 8/2009 | Kleiner et al. ............ 623/17.16 |
| 2010/0286784 A1* | 11/2010 | Curran et al. ............. 623/17.16 |

* cited by examiner

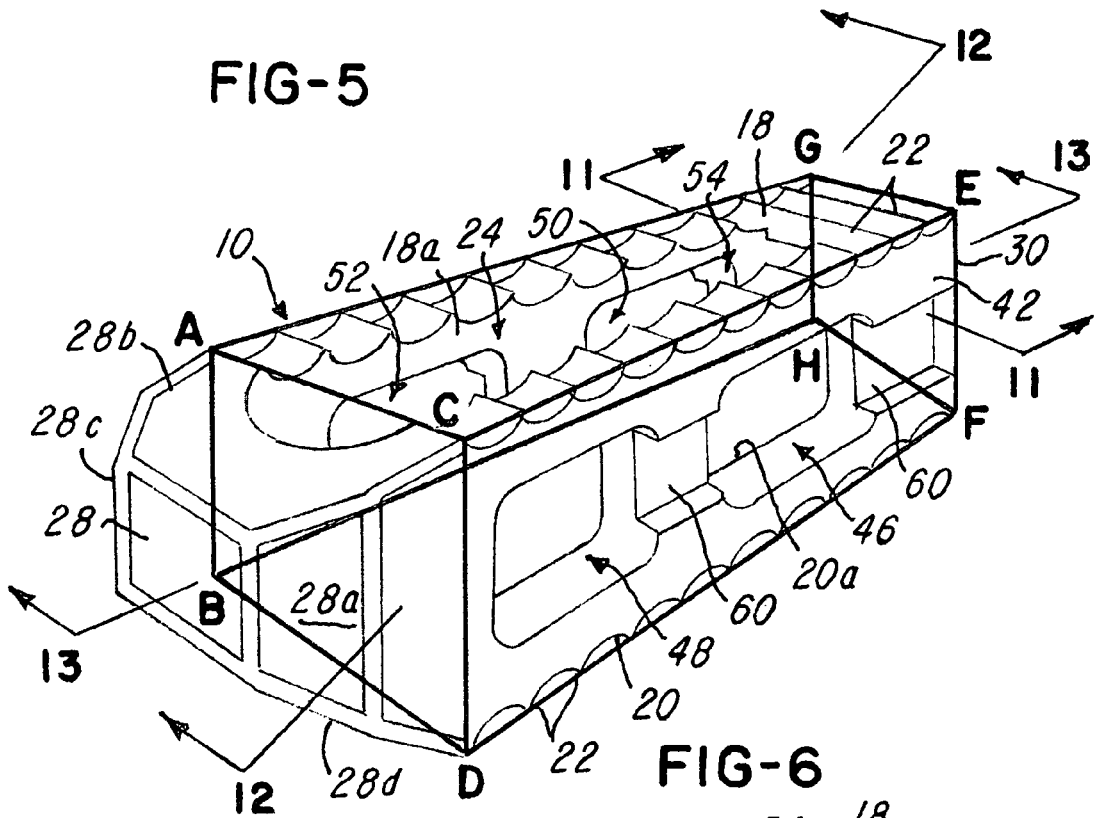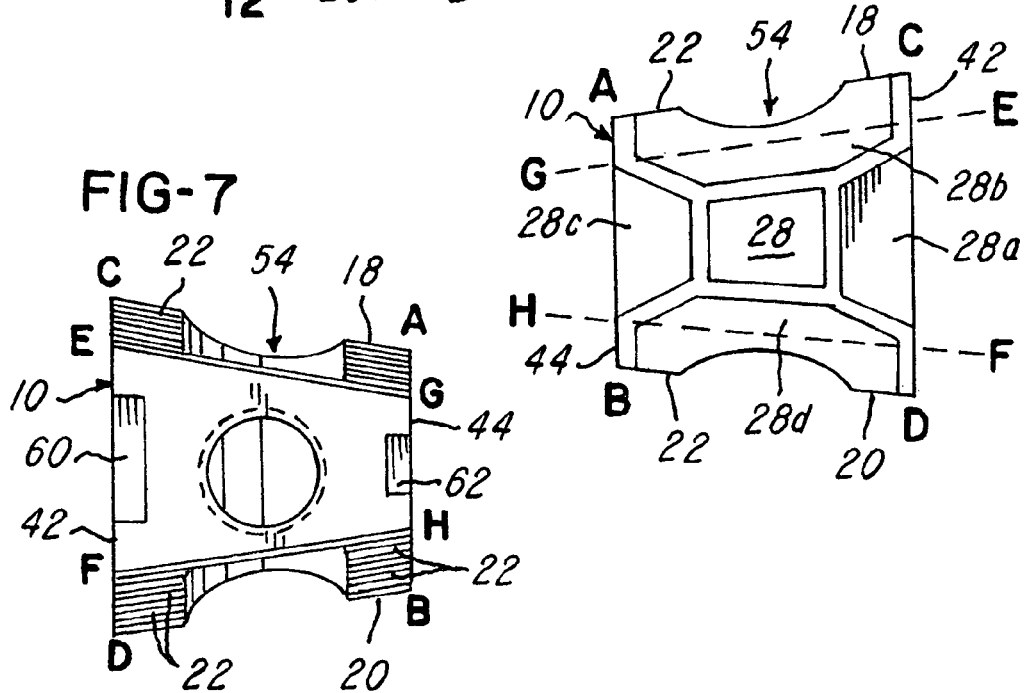

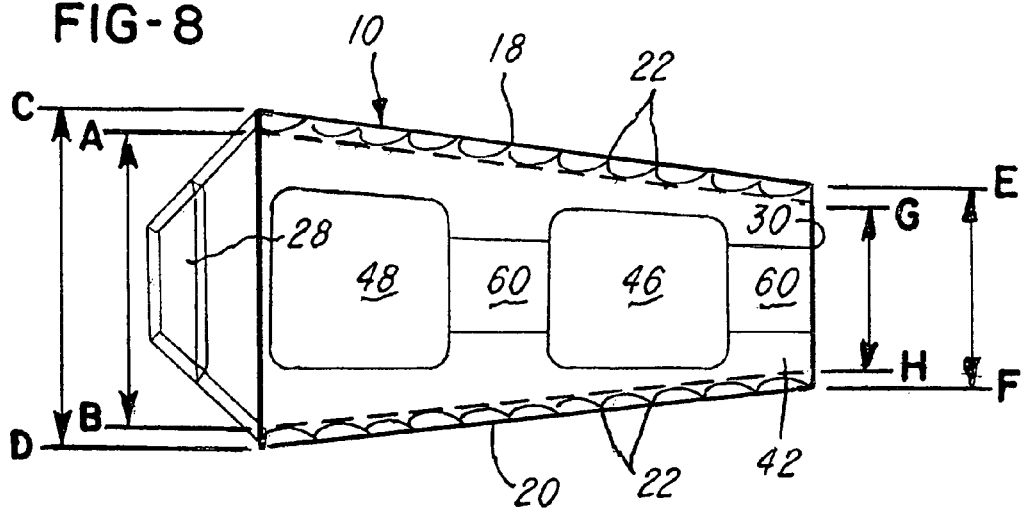
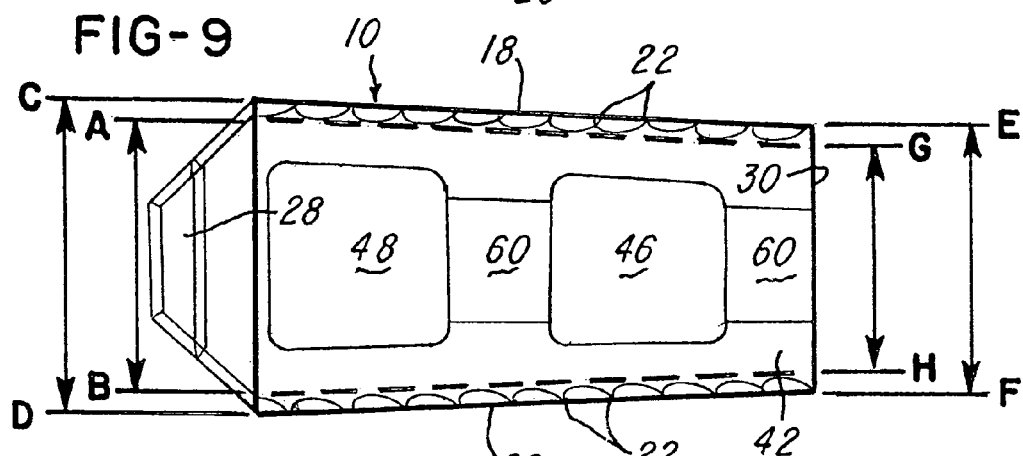
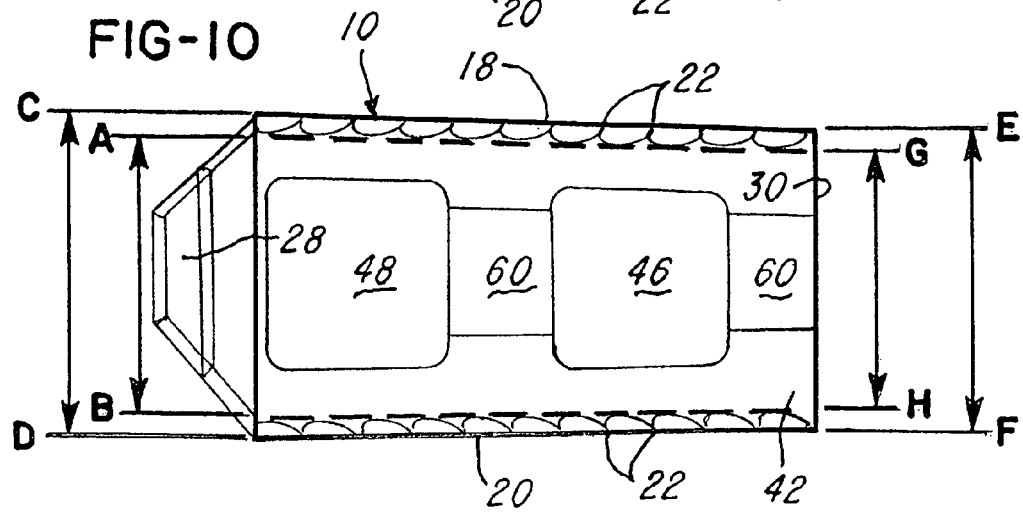

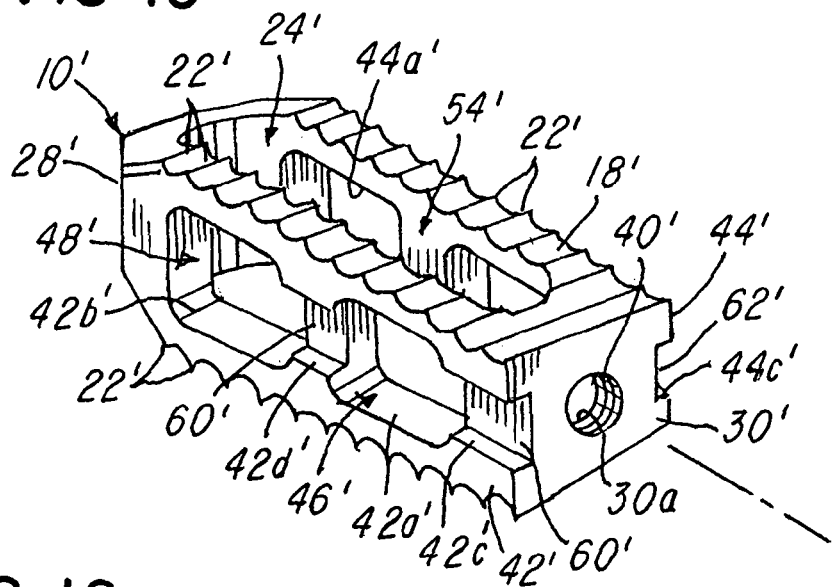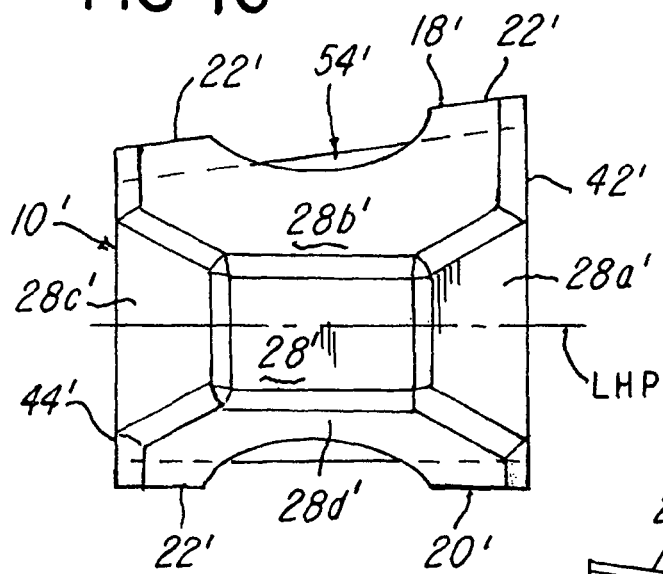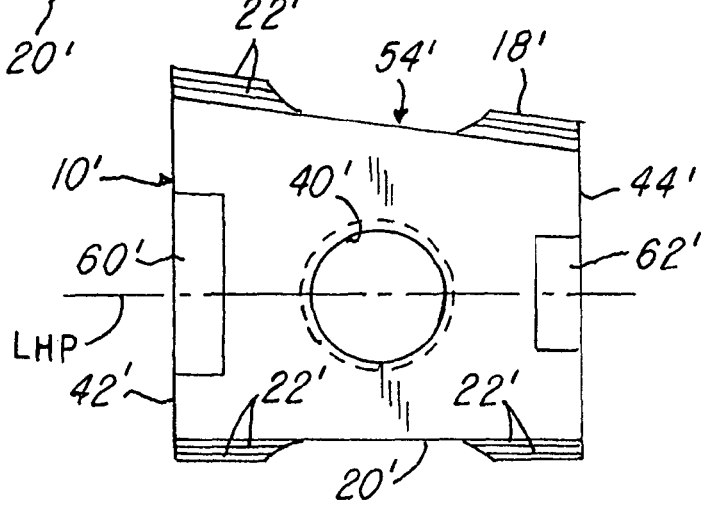

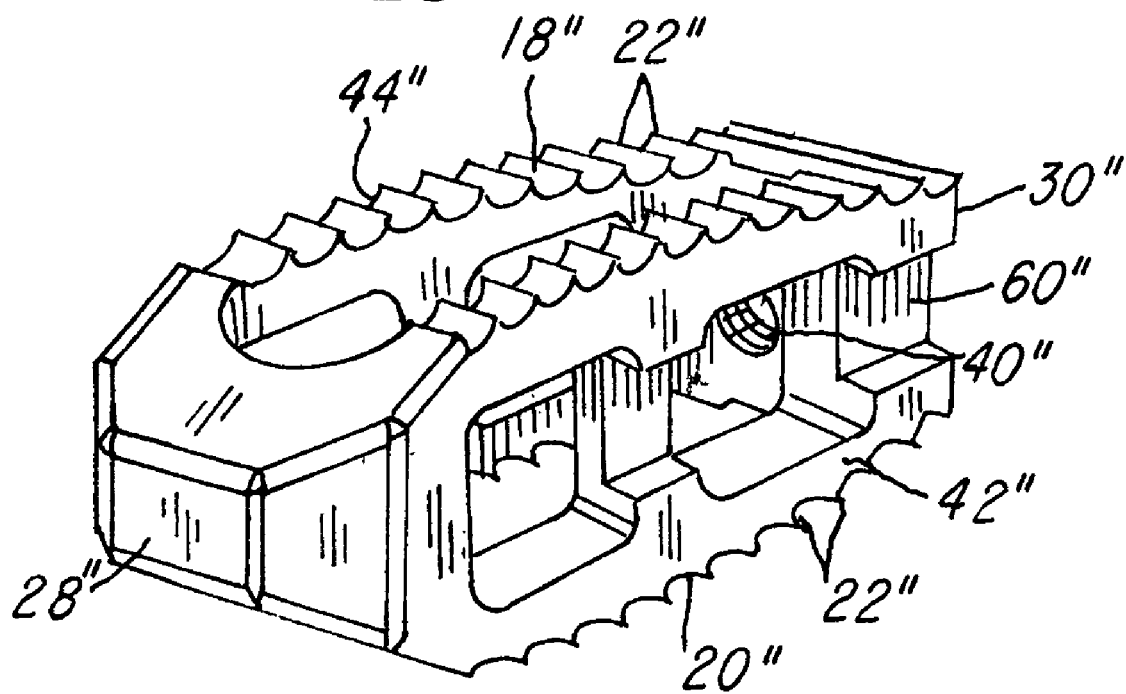

PROSTHETIC IMPLANT WITH BIPLANAR ANGULATION AND COMPOUND ANGLES

BACKGROUND OF THE INVENTION

1. Field of the Invention

This invention relates to a prosthetic implant, and more particularly, with a prosthetic implant having a biplanar angulation to permit insertion straight along a diagonal angle into a disk space.

2. Description of the Related Art

Spinal fusion is a commonly performed procedure. In a typical spinal fusion operation, a surgeon places a mechanical container, commonly known as a cage, between at least two adjacent vertebrae of the spine. This container contains or is later filled with bone graft which eventually incorporates into the adjacent vertebrae and creates a solid fusion. Interbody cages are placed in the disk space following removal of the disk. The cage can be surgically placed via several approaches, such as anteriorly through the abdomen, posteriorly through the spinal canal, posterolaterally through the neuroforamen of the vertebra, and transversely from a side of the spine. A goal of the surgical approach is to minimize trauma to adjacent structures and incision size.

A challenge to the placement of cages is the attainment of proper fitment between the adjacent vertebrae. It is important that a cage surface fits flushly against the endplates of the adjacent vertebrae. If a cage fits poorly, the cage could loosen, causing poor fixation and potential re-operation. The disk space, where the cage is placed, is not parallel. The space is angulated such that it is wider anteriorly than posteriorly. This angulation is termed lordosis.

Several cage designs have been proposed in the prior art. Brantigan (U.S. Pat. No. 4,834,757) describes a square shaped cage which is impacted in between vertebrae. Michelson (U.S. Pat. No. 5,015,247) describes a straight threaded cage which is screwed into the disk space. Brantigan (U.S. Pat. No. 5,425,772) and Michelson (U.S. Pat. No. 6,302,914) describe a cage with a built in single-plane lordotic angle to improve fitment between adjacent vertebrae. These cages are designed for posterior or anterior placement.

The placement of cages from posterior, lateral, and anterior approaches raise concerns about potential impingement upon important anatomical structures. Such structures are the spinal canal, the spinal nerves, and the abdominal vasculature, respectively. The posterolateral approach, also called the transforamenal approach, is gaining popularity as the preferred approach for the placement of intervertebral fusion cages. Typically, cages designed for this approach are "banana shaped," as exemplified by Varga, et al (U.S. Pat. No. 6,579,318).

A significant difficulty with banana-type cages is that their placement requires cage rotation at the time of placement to seat the cage in place. The cage is inserted at a 45 degree lateral angle into the disk space (the maximum angle limited by anatomical structures) and is then rotated a further 45 degrees within the disk space for proper placement. This rotational step is difficult in that it occurs blindly inside the disk space. Incomplete rotation frequently occurs, resulting in poor cage fitment, with potential loosening and reoperation.

If a Brantigan (U.S. Pat. No. 4,834,757) cage were inserted in a diagonal or non-straight trajectory, it would not have flush contact with the adjacent vertebrae due to the lordotic angle of the disk space. Furthermore, a standard lordotic cage, such as Michelson (U.S. Pat. No. 6,302,914), would have its lordotic angle in the incorrect orientation for proper fitment if placed diagonally.

What is needed is a cage that can be placed via the posterolateral approach in a straight manner and that does not require a further rotation for placement. Desirably, such a cage will be placed at a straight angle relative to an anterior-posterior axis and, preferably, at a diagonal or angle, such as approximately 45 degrees and reside in a diagonal configuration within the disk space.

SUMMARY OF THE INVENTION

Accordingly, one object of the invention is to provide a cage having a biplanar angulation.

Another object of the invention is to provide a cage that has a biplanar angulation and that may be inserted straight into a disk space, at an angle or diagonally relative to the anterior-posterior axis of the spine.

Still another object of the invention is to provide a cage having a biplanar angulation and that minimizes or eliminates the need for rotation after the cage is inserted into the disk space.

Yet another object of the invention is to provide a cage having lateral slots or channels for insertion of a tool or instrument to facilitate placement of the cage.

In one aspect, this invention comprises a fusion cage comprising a cage body having a plurality of surfaces, the plurality of surfaces cooperating to define a multi-planar angulation adapted to achieve substantially flush fitment in a disk space between adjacent vertebrae when the fusion cage is inserted in the disk space.

In another aspect, this invention comprises a method for fusing bones, the method comprising the steps of providing a cage adapted to be inserted into a disk area substantially diagonally or in an angled direction with respect to an anterior-posterior axis, the cage having a first surface lying in a first plane and a second surface lying in a second plane, and inserting the cage in the substantially diagonal or angled direction such that the first and second surfaces engage a surface of a first vertebrae and a second vertebrae substantially flush.

These and other objects and advantages of the invention will be apparent from the following description, the accompanying drawings and the appended claims.

BRIEF DESCRIPTION OF THE ACCOMPANYING DRAWINGS

FIG. 5 is a perspective view of the cage with various projection lines showing the dimensional relationships between the various line segments to illustrate the biplanar angulation or compound angles formed by the various surfaces of the cage;

FIG. 6 is a front view of the cage;

FIG. 7 is a rear view of the cage;

FIG. 8 is a side view of the cage shown in FIG. 1, showing the various relationships and dimensions and relative dimensions of the various corners of the cage;

FIGS. 9 and 10 are illustrative embodiments showing different multi-planar or biplanar angulations;

FIG. 15 is a perspective view of yet another embodiment of the cage of FIG. 1;

FIG. 16 is a front view of the cage;

FIG. 17 is a rear view of the cage;

FIG. 23 is a is a perspective view of another embodiment of the invention.

DETAILED DESCRIPTION OF THE PREFERRED EMBODIMENTS

Figure 1:
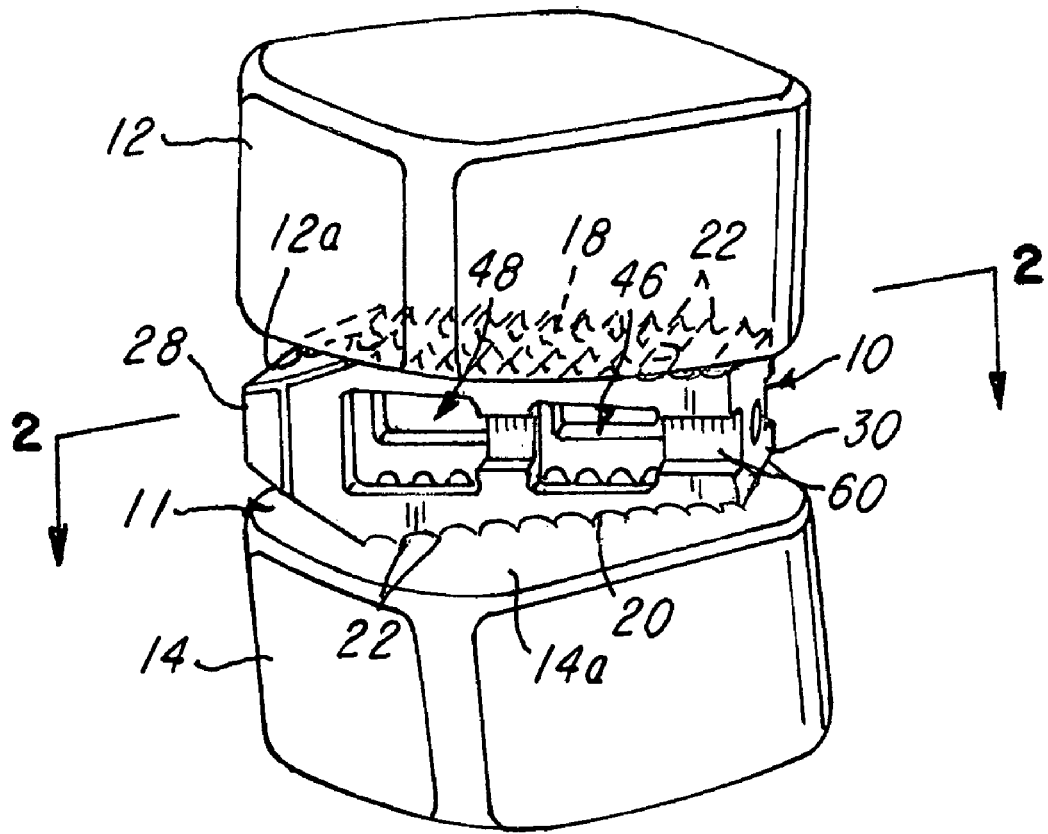
FIG. 1 is a perspective view of a cage in accordance with one embodiment of the invention showing the cage placed in a disk space.

Referring now to FIGS. 1-10, a prosthetic implant or fusion cage 10 is shown for insertion and use in a disk space or disk area 11 between a first vertebra 12 and second vertebra 14. In the illustration being described, the first vertebra 12 has a first or superior surface 12a and the second vertebra 14 has a second or inferior surface 14a, as best illustrated in FIG. 1. The cage 10 is inserted straight posterolaterally, also called a transforamenal approach, into the disk area 11 between the first vertebra 12 and second vertebra 14. As described and shown, the cage 10 is inserted on a diagonal or angled direction with respect to an anterior-posterior axis AP (FIG. 2), such as in the direction of arrow 16 as shown.

Figure 3:
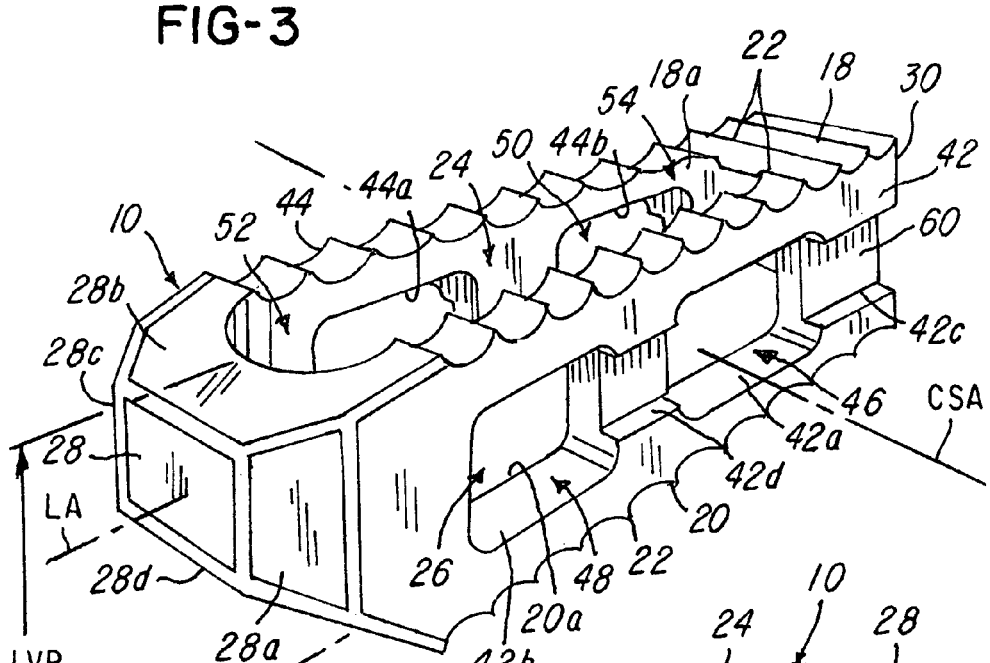
FIG. 3 is a perspective view showing various details of the cage shown in FIGS. 1 and 2.
Figure 4:
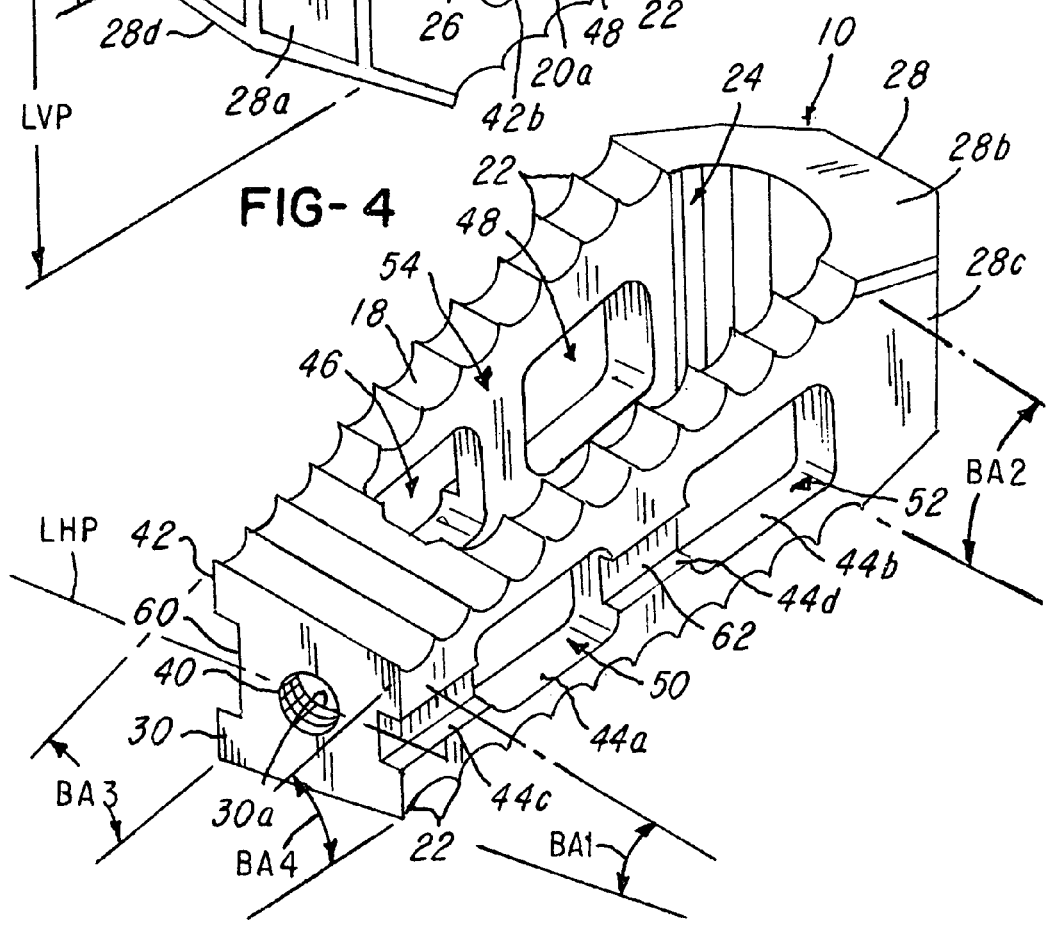
FIG. 4 is another perspective view of the cage of FIG. 1.

Notice in FIGS. 3 and 4 that the cage 10 comprises a superior or top surface 18 and a generally opposing inferior or bottom surface 20. In the illustration being described, note that the surfaces 18 and 20 are serrated or comprise teeth 22 to facilitate preventing the cage 10 from loosening or becoming displaced after the cage 10 is placed in the disk area 11 between the first vertebra 12 and the second vertebra 14. The cage 10 is adapted or configured to comprise the surfaces 18 and 20 that cooperate to define a biplanar angulation and that cooperate to define multiple angles or at least one compound angle as described herein. The relative angulation between surfaces 18 and 20 facilitate full or flush surface contact between the vertebrae surfaces 12a and 14a and the surfaces 18 and 20, respectively, of the cage 10.

As illustrated in FIGS. 3 and 4, the surfaces 18 and 20 comprise an interior wall 18a and 20a, respectively, that define generally oval apertures or openings 24 and 26, for receiving bone graft material. Note that the cage 10 further comprises a front portion, surface or end 28 and a rear surface or end 30 as shown. The front portion, surface or end 28 comprises a plurality of angled surfaces 28c and 28d, as shown, that cooperate to define a nose, prow or angled frontal portion for ease of substantially straight or linear insertion and placement into the disk area 11 using a posterolateral or transforamenal approach.

The rear surface or end 30 comprises an interior wall 30a having a threaded aperture 40 for receiving an instrument or bone graft material after the cage 10 is inserted substantially straight or linearly into the disk area 11 using the posterolateral or transforamenal approach.

The cage 10 further comprises a side or third surface 42 and a generally opposing side or fourth surface 44 as shown. Note that the third surface 42 comprises a plurality of interior walls 42a and 42b that define apertures 46 and 48, respectively. Similarly, fourth surface 44 comprises interior walls 44a and 44b that define apertures 50 and 52, respectively, as shown. As illustrated, the apertures 46 and 48 are generally opposed to the apertures 50 and 52, respectively, and provide lateral openings adapted to permit graft material to be inserted into an open cage area 54 for fusing the vertebrae 12 and 14 together. Thus, it should be understood that the bilateral openings or apertures 46, 48, 50 and 52 facilitate insertion of bone graft material (not shown) and for bone ingrowth. The inferior and superior openings 24 and 26 further facilitate bone ingrowth.

Figure 14:
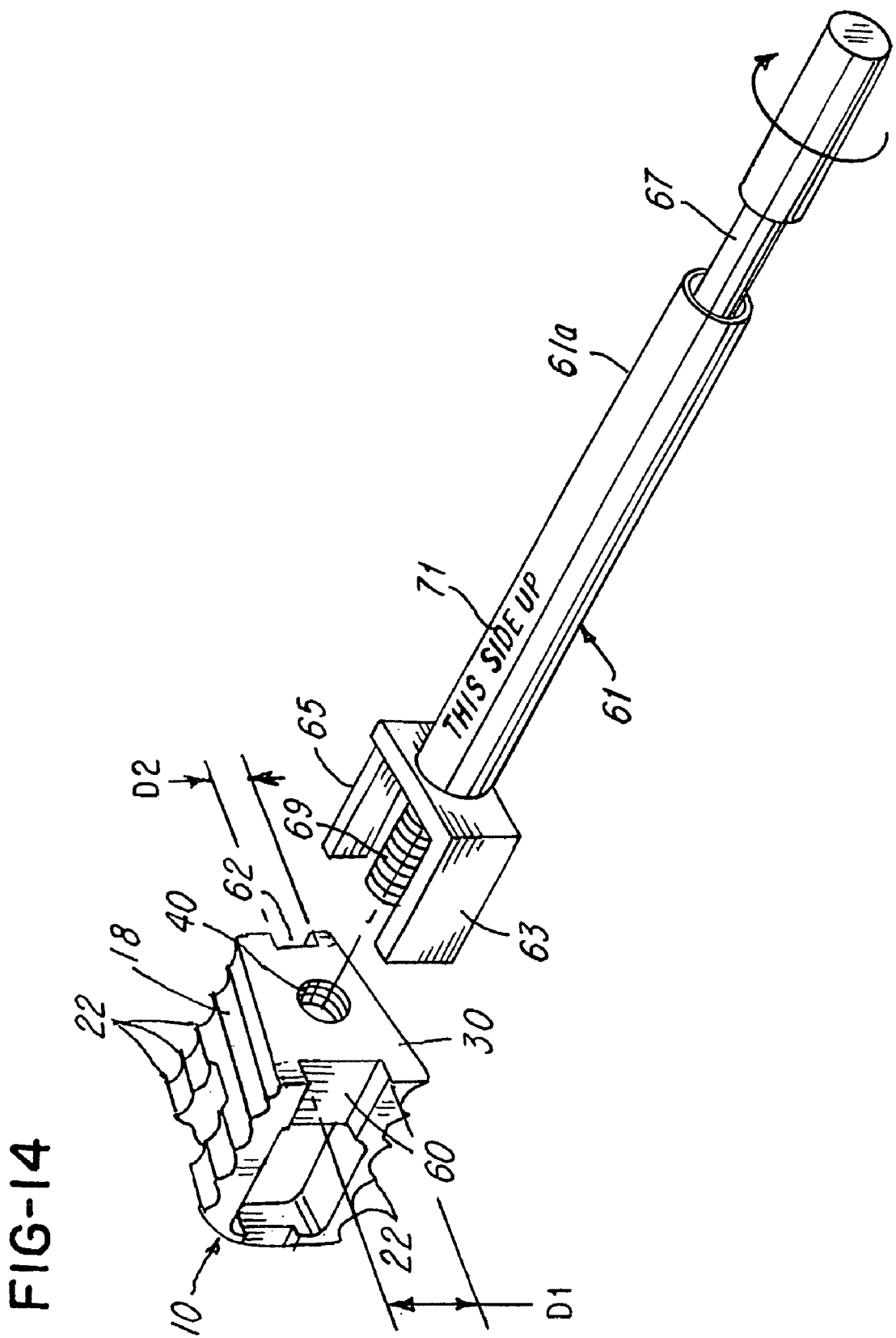
FIG. 14 is a fragmentary exploded perspective view of a portion of a cage and an insertion tool.

The surfaces 42 and 44 each comprise a plurality of generally U-shaped walls or surfaces 42c, 42d and 44c, 44d, respectively, to define a first lateral slot 60 and a second lateral slot 62, respectively, for facilitating the placement of the cage 10 using an insertion tool or a surgical instrument 61 (FIG. 14). Notice that the lateral slots 60 and 62 are asymmetrical to allow for directional coupling to an insertion tool or surgical instrument 61. In this regard, notice that the slot 60 has a dimension D1 that is greater than a dimension D2 of the slot 62. The lateral slots 60 and 62 are adapted to receive a generally complementary shaped inter-fitting members or projections 63 and 65, respectively, of the insertion tool or surgical instrument 61.

The insertion tool or surgical instrument 61 has a hollow tubular portion 61a that receives a rotatable shaft extension 67 having an end 69 that is threaded so that it can be screwed or threaded into the threaded aperture 40, as illustrated. During use, the surgeon would place the rotatable shaft extension 67 until the cage 10 becomes secured or fixed to the insertion tool or surgical instrument 61.

After placement of the cage 10, the rotatable shaft extension 67 is rotated counterclockwise from the cage 10. Note that the insertion tool or surgical instrument 61 or tubular portion 61a may have indicia 71 for indicating to the surgeon or user the proper orientation of the cage 10, thereby reducing or eliminating the chance that the cage 10 would be improperly placed, for example, upside down into the disk area 11.

Referring now to FIGS. 3-10, the relative relationship of the surfaces 18 and 20, multiplanar or biplanar angulation and compound angle(s) they define will now be described. For ease of illustration, FIGS. 5-10 show various line projections or line segments corresponding to lines or segments between various boundary corners or points or edges of the cage 10. The points are identified and labeled with the letters A-F. The various relationships between and/or among the line segments and other segments will be used for ease of understanding to illustrate or demonstrate the biplanar angulation or compound angles of the cage 10 in this illustration. The ">" designation is understood to mean that a dimension of a segment is larger than the dimension of the segment(s) to which it is compared, "<" means the dimension is less, and "=" means the dimension of the segments is equal. For example, "CD>AB" means that the portion of the cage 10 associated with line segment CD comprises a dimension that is greater than the portion of the cage 10 associated with segment AB.

Returning to the description in the illustration of FIGS. 5-8, note that the line segment length C-D>A-B>E-F>G-H, and the area defined by ACDB in FIG. 5 is greater than the area GEFH. As illustrated in FIGS. 5-8, the dimension between the line segments A-C and B-D gets smaller when moving from line C-D to A-B. Likewise, the cage 10 has a compound or biplanar angulation so that a cross-sectional height dimension (as viewed in FIG. 5) of the cage 10 gets smaller from segment C-D as it moves to every other segment A-B, G-H and E-F.

Figure 5A:
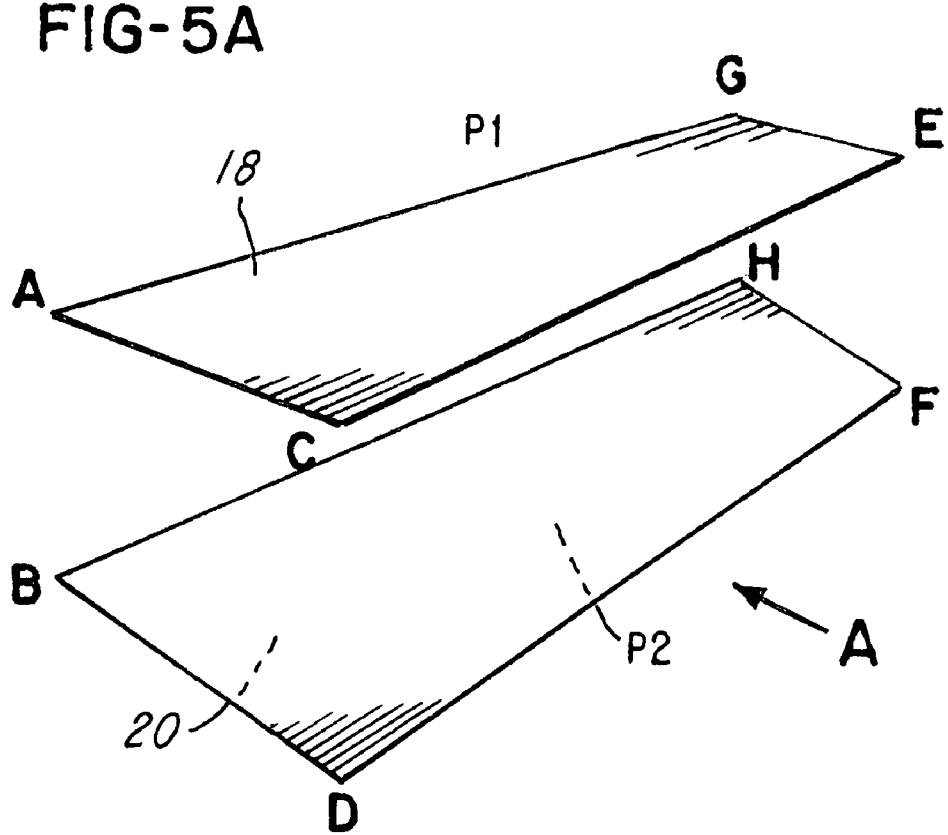
FIG. 5A is view showing imaginary planes corresponding to the superior and inferior surfaces of the cage, showing their relative relationship and multi-planar or bi-planer angulation.
Figure 5B:
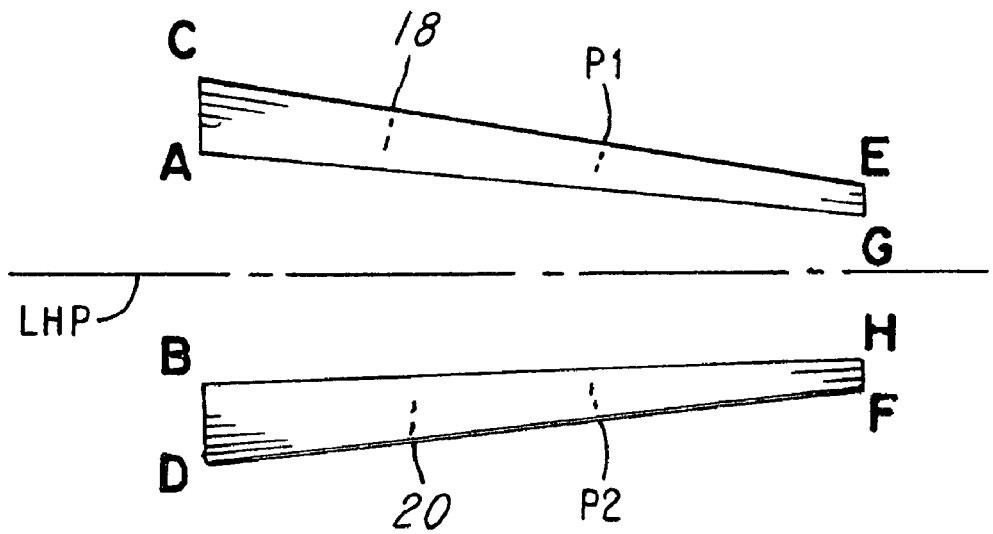
FIG. 5B is a view, taken in the direction of arrow A in FIG. 5A, showing the relationship of the planes and biplanar angulation of the surfaces.

FIG. 5A illustrates imaginary planes P1 and P2 in which the surfaces 18 and 20, respectively, lie. FIG. 5B shows a view taken in the direction of arrow A in FIG. 5A and generally perpendicular to the plane P2 showing the biplanar angulation or relative tilt (when viewed from left to right in the FIG. 5B and toward G-H). In the example, the surfaces 18 and 20 converge along both a longitudinal axis from a first point, such as the end 28, to a second point such as the rear surface or end 30. The planes P1 and P2 and surfaces 18 and 20 also converge in a direction from segment C-D to G-H in the illustration and also when viewed in a direction generally perpendicular to that longitudinal axis as shown in FIGS. 5-A, 5B and 5C. Thus, the cage 10 and surfaces 18 and 20 define numerous angles, such as angles BA1, BA2, BA3 and BA4 shown in FIG. 4. The angles are all different in the illustration.

Figure 11:
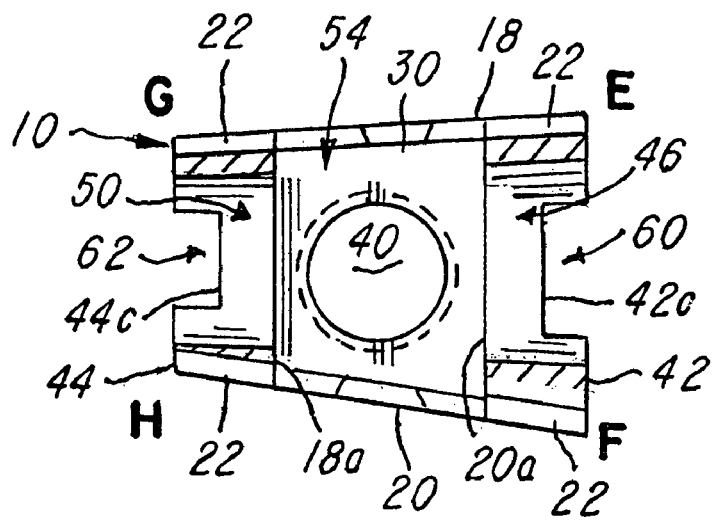
FIG. 11 is a cross-sectional view taken along the line 11-11 in FIG. 5.
Figure 12:
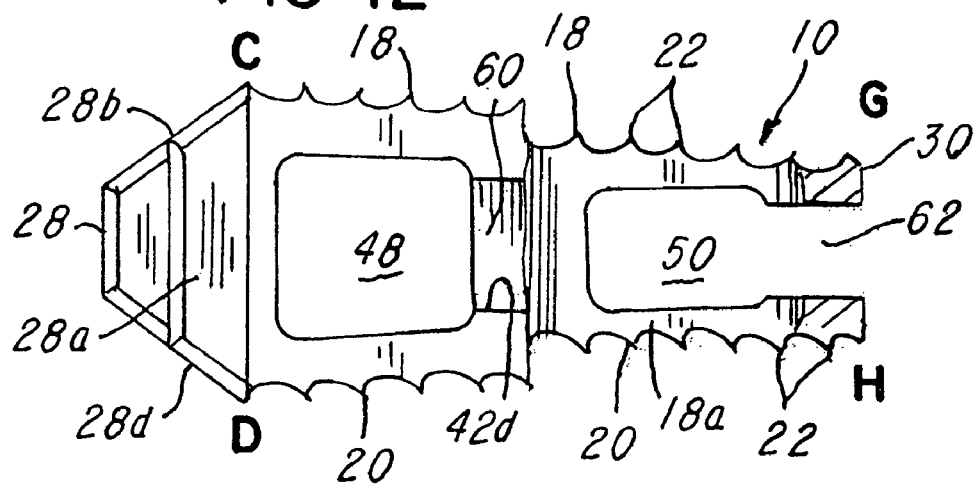
FIG. 12 is a diagonal view taken along the line 12-12 in FIG. 5.
Figure 13:
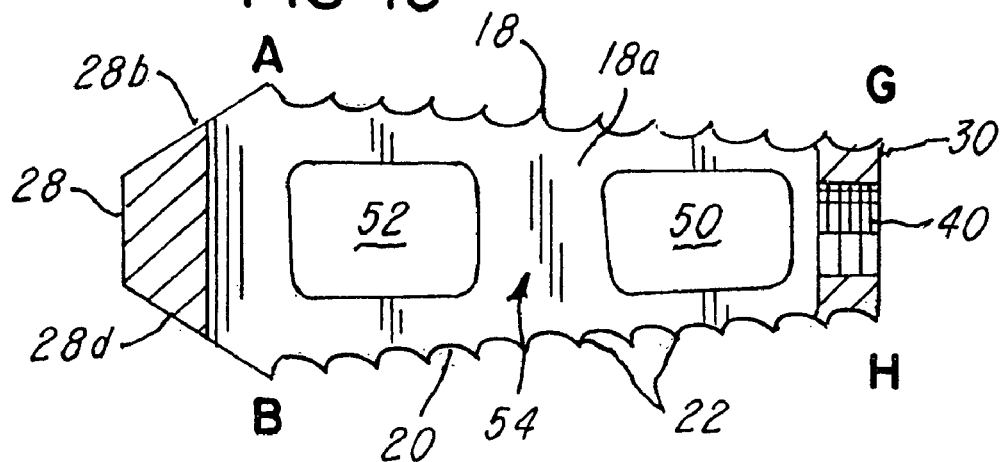
FIG. 13 is a sectional view taken along the line 13-13 in FIG. 5.

Stated another way, the cage 10 comprises a longitudinal axis LA (FIG. 3) and a cross-sectional axis CSA (FIG. 3) that is generally perpendicular to the longitudinal axis LA. In the illustration being described in FIGS. 1-14, the cage 10 is symmetrical about a longitudinal horizontal plane LHP (FIG. 4) along the longitudinal center axis (FIG. 3), but is non-symmetrical in a longitudinal vertical plane LVP (FIG. 3). In one illustration, the cage 10 assumes a trapezoid (FIG. 11) in a vertical cross-sectional plane that is generally perpendicular to the longitudinal center axis, such as the imaginary plane along line 11-11 in FIG. 5. It should be understood, however, that the cage 10 could assume another shape, such as a trapezium (see FIGS. 15-19B), ellipsoid, circular, oval, arcuate or other shape. Other illustrative embodiments are shown in FIGS. 15-23 described later herein.

One important feature of the cage 10 is that the opposing surfaces 18 and 20 in the illustration provide, are arranged or are adapted to cooperate to define one or more compound angles or a biplanar angulation so that the surfaces 18 and 20 become in substantially flush contact with the surfaces 12a and 14a, respectively, when the cage 10 is inserted substantially straight or linearly on a diagonal or angle into the disk area 11 using a posterolateral or transforamenal approach and, if necessary, rotated as described herein.

FIG. 8 is an illustration corresponding to the embodiments of FIGS. 3-7 illustrating CD being greater than AB which is greater than EF which in turn is greater than GH. It should be understood, however, that the degree of the biplanar angulation or compound angle will be selected or changed and will depend upon the relative relationship or orientation between the disk surfaces 12a and 14a. Several other illustrative embodiments are shown in FIGS. 9-10. For example, FIG. 9 illustrates an embodiment wherein the cage 10 has dimensions such that the line segment CD>AB=EF>GH. FIG. 10 illustrates an embodiment where line segment CD>AB<EF>GH. As described later herein, the user will select the cage 10 having the desired biplanar angulation in response to the disk area 11 and the relative relationship of the vertebrae surfaces 12a and 14a. This selection and placement will now be described.

During a surgical procedure it should be understood that the cage 10 is inserted generally straight or linearly at an angle or on a diagonal trajectory relative to the anterior-posterior axis AP (FIG. 2) using a posterolateral or transforamenal approach. As mentioned, the cage 10 and the biplanar angulation or compound angle(s) defined by surfaces 18 and 20 will be selected and adapted depending upon the relative relationship between the surfaces 12a and 14a. In general, the angle Θ (FIG. 2) of insertion increases, the length differences between the segments EF-CD will be decreased and the length differences between the segments AB-GH will also be decreased or lesser. In one embodiment, the cage is being rotated from an angle parallel to the intervertebral lordotic angle to an angle perpendicular to the intervertebral lordotic angle. Segments EF-CD and AB-GH no longer have to conform to this lordotic angle in this trajectory and therefore their length differences are decreased.

As a size of the cage 10 increases, a length difference, for example, between segments EF-CD will be greater as the cage 10 gets larger because a larger amount of the lordotic angle is covered by the cage, and segments or dimensions AB-GH will also be greater. FIGS. 20A-20D, 21A-21D and 22A-22D further illustrate these concepts. All else being equal, larger cages 10 require larger segment differences. A tiny cage 10 covers very little length of the lordosis, so the difference in side length will be small.

Figure 20A:
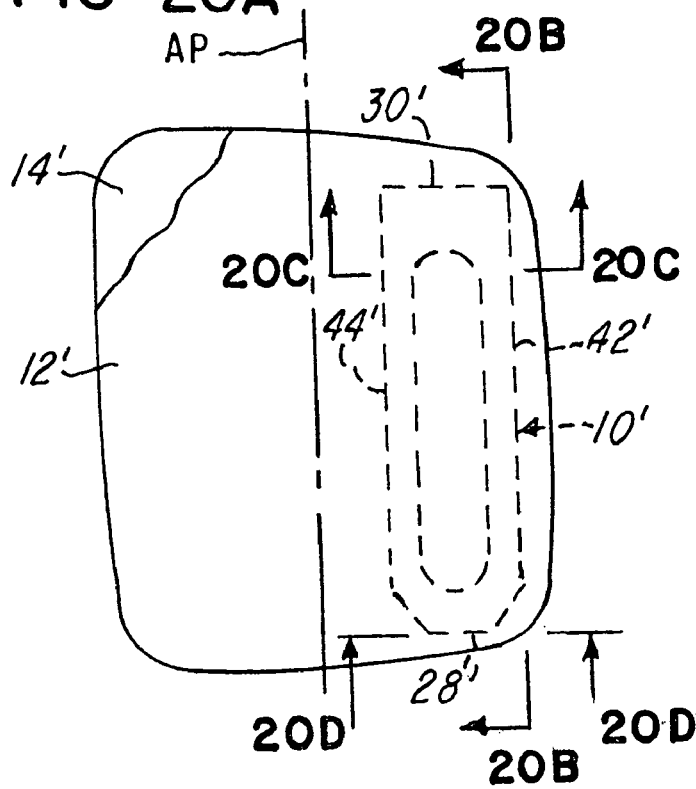
FIG. 20A illustrates a cage placed in a space between two disks.
Figure 20B:
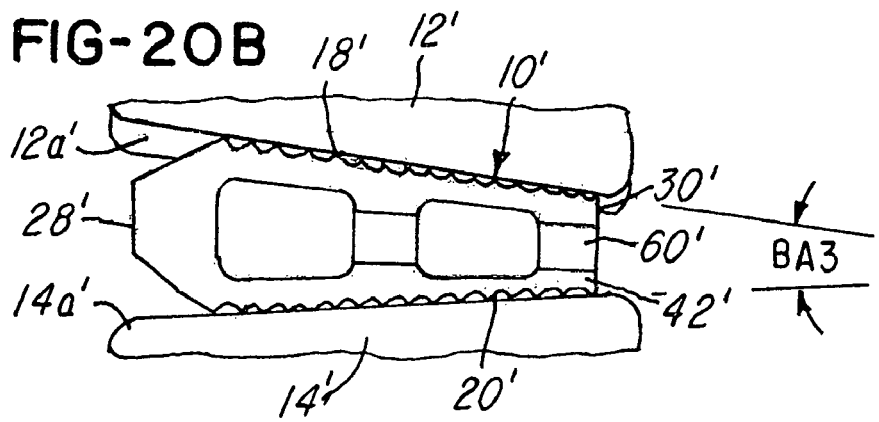
FIG. 20B is a view taken along line 20B-20B of FIG. 20A.
Figure 20C:
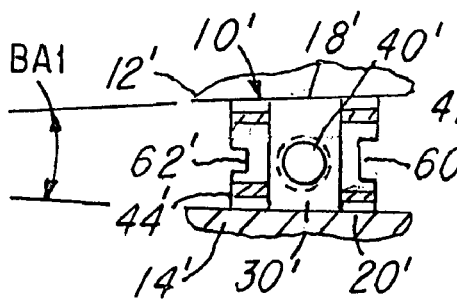
FIG. 20C is a view taken along line 20C-20C of FIG. 20A.
Figure 20D:
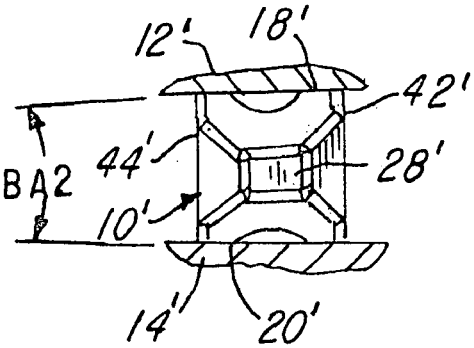
FIG. 20D is a view taken along line 20D-20D of FIG. 20A.
Figure 21A:
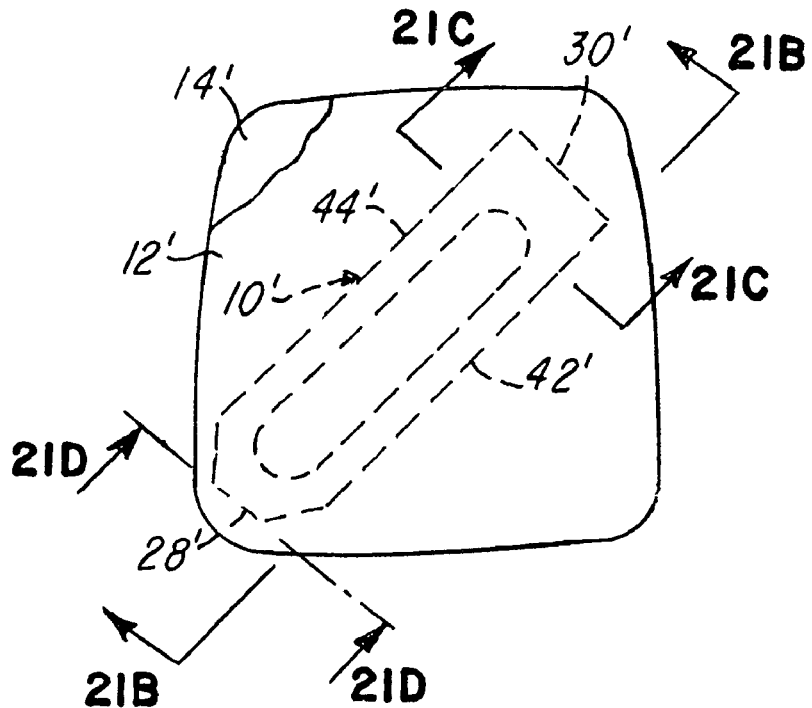
FIG. 21A is a view similar to FIG. 20A showing use of another cage.
Figure 21B:
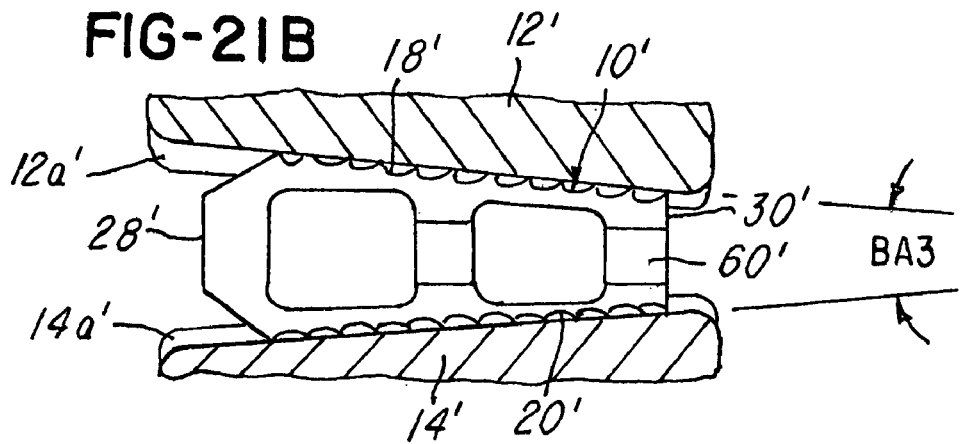
FIG. 21B is a view taken along line 21B-21B of FIG. 21A.
Figure 21C:
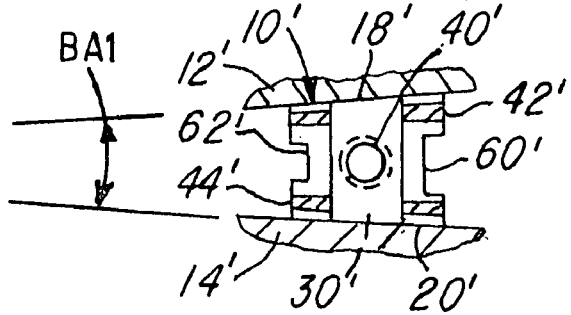
FIG. 21C is a view taken along line 21C-21C of FIG. 21A.
Figure 21D:
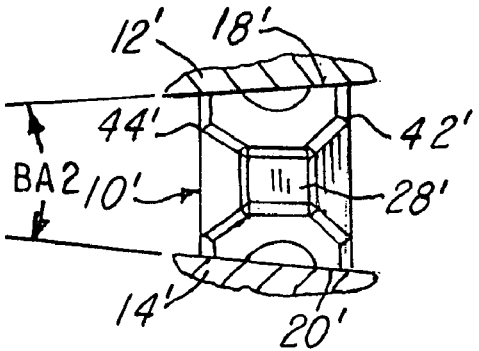
FIG. 21D is a view taken along line 21D-21D of FIG. 21A.

In the illustration in FIGS. 20A-20D, a selected cage 10 is inserted using a posterolateral or transforamenal approach and rotated such that its longitudinal axis is generally parallel to the anterior-posterior axis AP as shown. In this illustration, the cage 10 may have a relatively large longitudinal angulation (the angulation BA3 associated with side 42) as illustrated in FIG. 20B. Note, however, that the surfaces 12a and 14a in the illustration are angled not only posterolaterally, but also slightly in a lateral direction (i.e., along a cross-sectional angulation that is generally perpendicular to the longitudinal axis of the cage 10), as illustrated in FIG. 20B. Given the slight angulation, the cage 10 may have only a slight cross-sectional angulation (that is, the angles BA1 and BA2, illustrated in FIGS. 20C and 20D, respectively).

FIGS. 21A-21D illustrate a similar relationship between surfaces 12a and 14a. However, note that the cage 10 is inserted and rotated or pivoted such that it is angled with respect to the anterior-posterior center line. In view of this positioning, note that the user may select a cage 10 wherein the surfaces 12a and 14a define the angle BA3 that is less than the angle BA3 associated with the embodiment illustrated in FIG. 20B. Note that the cross-sectional dimension (i.e., those angles BA1 and BA2 illustrated in FIGS. 21C and 21D) will be slightly larger than those corresponding angles illustrated in FIGS. 20C and 20D, as shown.

FIGS. 22A-22D show another extreme placement of the cage 10, wherein the cage 10 is situated such that its longitudinal axis is generally perpendicular to the anterior-posterior axis. In this position, note that the longitudinal angle is associated with the side 42 (that is, the angle BA3 in the illustration), but generally corresponds to the angle (labeled DA in FIG. 22B) defined by the disk surfaces 12a and 14a. Compare this cage 10 to the cage 10 in the illustration described earlier herein relative to the embodiment of FIG. 20B. Note the cage 10 is selected and adapted to conform to the relationship of the surfaces 12a and 14a as well as the position in which the cage 10 is going to be inserted into the disk area 11 between the surfaces 12a and 14a.

Figure 22A:
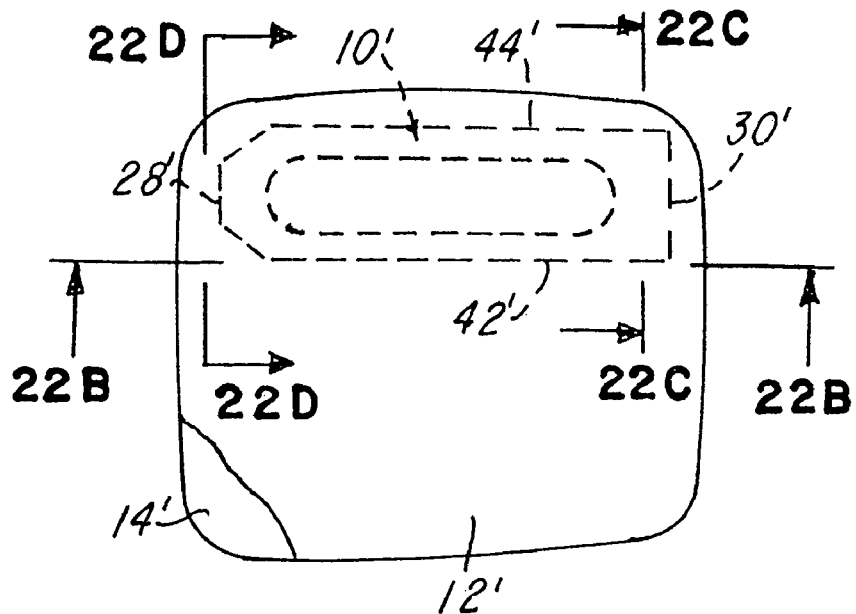
FIG. 22A is a view similar to FIGS. 20A and 21A.
Figure 22B:
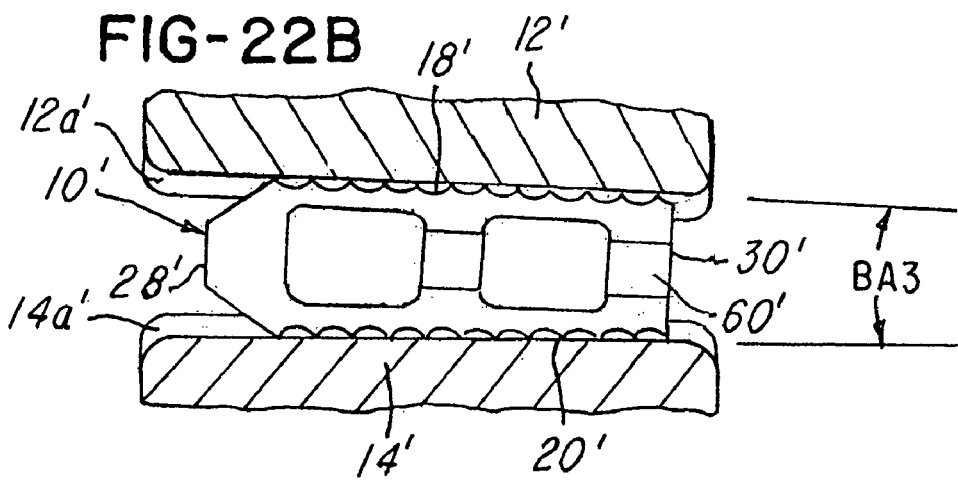
FIG. 22B is a view taken along line 22B-22B of FIG. 21A.
Figure 22C:
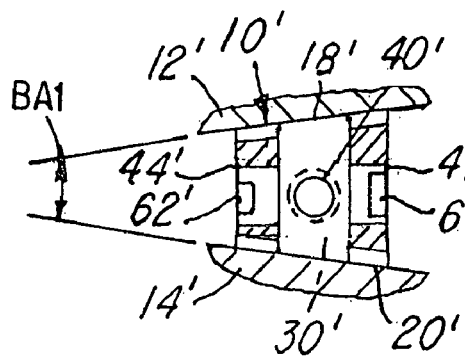
FIG. 22C is a view taken along line 22C-22C of FIG. 21A.
Figure 22D:
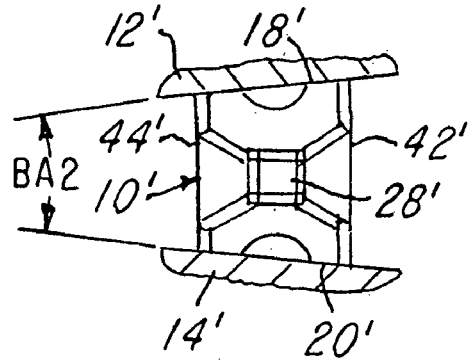
FIG. 22D is a view taken along line 22D-22D of FIG. 21A.

Continuing with the illustration, a cage 10 is shown in FIGS. 22A-22D, having a longitudinal angulation that is slight, as illustrated in FIG. 22B, given the lateral placement of the cage 10 in the disk area 11. However note that the cross-sectional angulation and angles BA1 (FIG. 22C) and BA2 (FIG. 22D) may be relatively greater when compared to the same angles illustrated in FIGS. 20C and 20D.

Advantageously, the implant, system and method provides means for adapting and selecting a cage 10 in response to the relationship between the surfaces 12a and 14a as well as the placement of the cage 10 using a posterolateral approach and the position of the cage 10 in the disk area 11. In some cases, it may be necessary to use a cage 10 having larger or smaller longitudinal angles BA3 and BA4 and smaller cross-sectional angles BA1 and BA2, while in other environments it may be desired to use a cage 10 having relatively larger cross-sectional angles BA1 and BA2 and smaller biplanar angles BA3 and BA4. The angles BA1 and BA2 can be changed relative to each other as can angles BA3 and BA4.

Thus, it should be appreciated that the invention provides a cage 10 having biplanar and angulation defining compound angles that can adapt to various environments such that the surfaces 18 and 20 provide a snug fit against the surfaces 12a and 14a, respectively.

As alluded to earlier herein, the cage 10 could assume different shapes, such as trapezium, ellipsoid, circular, oval, arcuate or other shapes. In this regard, and as described earlier herein, the embodiment of FIGS. 1-14 illustrate a cage 10 that is generally symmetrical about the longitudinal horizontal plane (FIG. 4). FIGS. 15-19B illustrate another embodiment, similar to the embodiment in FIGS. 1-14 wherein the cage 10 is not symmetrical about the longitudinal horizontal plane as illustrated in FIGS. 15-17. The parts in this embodiment are the same or similar to the parts in the embodiments of FIGS. 1-14 and those same or similar parts have been identified with the same part numbers, except that a prime mark ("'") has been added to the part numbers of the embodiment shown in FIGS. 15-19B.

In this illustrative embodiment, the cage 10 is not symmetrical about the longitudinal horizontal plane LHP illustrated in FIGS. 16 and 17, and the surfaces 18, 20, 42 and 44 cooperate to define a trapezium in cross-section as shown.

Figure 18:
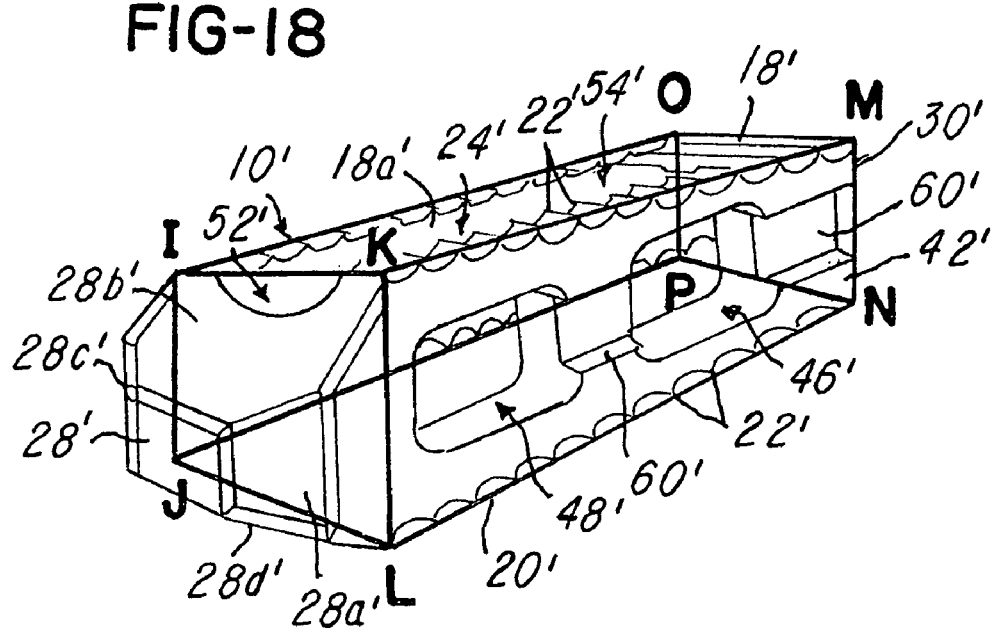
FIG. 18 is a perspective view of the cage similar to FIG. 5.

As illustrated in FIG. 18 and as with the embodiment being described earlier herein, various relationships between the segments may be defined. For example, as illustrated in FIGS. 15-18, the line segment KL is greater than IJ is greater than MN is greater than OP and the area defined by IKLJ in FIG. 18 is greater than the area OMNP. As with the prior embodiment, these various dimensions and relationships may be changed, modified or adapted to the particular environment or disk area 11 in which the cage 10 is going to be used.

Figure 19A:
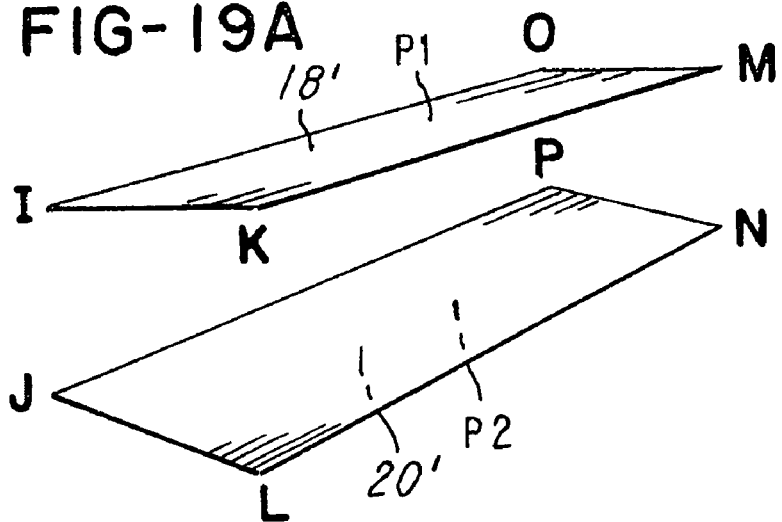
FIGS. 19A and 19B are views similar to FIGS. 5A and 5B, respectively.
Figure 19B:
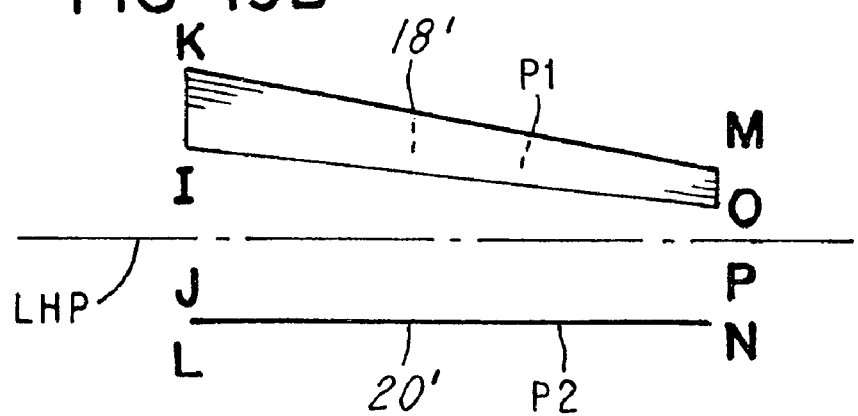

FIGS. 19A-19B are similar to the imaginary planes shown in FIGS. 5A and 5B. These planes, however, show the non-symmetry of the surfaces 18 and 20 about the longitudinal horizontal plane. By comparison, note the planes P1 and P2 illustrated FIG. 5B show the planes P1 and P2 being generally symmetrical about the longitudinal horizontal plane. As with the prior embodiment, the cage 10 in FIG. 15 is also asymmetrical about the longitudinal plane.

FIG. 23 illustrates yet another embodiment of the invention illustrating a different shape of the cage 10 having biplanar angulation. In this embodiment, the surfaces 18 and 20 are bowed, convex or arcuately shaped as shown. Similar parts are identified with a double prime mark.

Thus, it should be understood that the cage 10 is selected and/or adapted to comprise a biplanar angulation and to permit a posterior-lateral insertion into the disk area 11. The cage 10 is selected or adapted such that it will provide a flush fitmet in a lordotic disk space when placed diagonally via a posterolateral approach. Advantageously, the cage 10 provides biplanar angulation to allow for full surface contact with the surfaces 12a and 14a of the adjacent vertebrae 12 and 14, respectively, when placed at the angled or diagonal trajectory. Note that the cage 10 is inserted in the angled or diagonal trajectory and that the superior and inferior cage surfaces 18 and 20 are in flush or substantially flush engagement with the surfaces 12a and 14a.

It should be understood that while the embodiments illustrated in FIGS. 1-10 show a polygonal or multi-sided shaped cage 10, the cage 10 could take other configurations, such as elliptical, circular or the like. The important feature is that the cage 10 is adapted to provide a biplanar angulation of surfaces 18 and 20 that cooperate to define a compound angle or a biplanar angulation that facilitate a generally or substantially flush fit against surfaces 12a and 14a, respectively, of the vertebrae during generally straight insertion using a posterior lateral approach.

Figure 2:
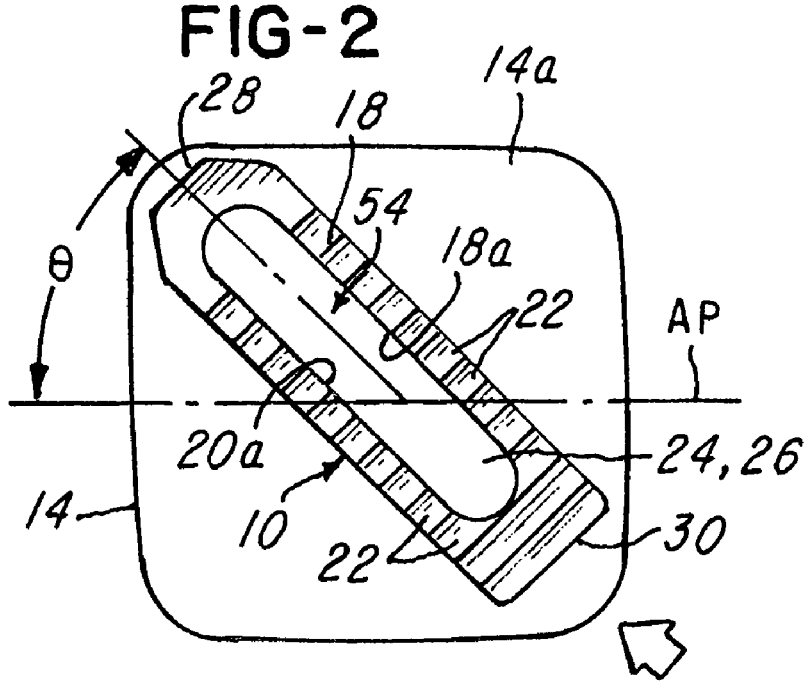
FIG. 2 is a view, taken along the line 2-2 in FIG. 1, showing the cage inserted straight and at a diagonal or an angle with respect to an anterior-posterior axis.

During use, the insertion tool or surgical instrument 61 (FIG. 14) is screwed to the cage 10 as illustrated in FIGS. 1 and 2, the cage 10 is placed using a posterolateral or transforamenal approach and inserted into the disk area 11 (FIG. 1) in a generally straight or linear manner. In the illustration being described, the cage 10 provides means and apparatus that can be placed via a posterolateral approach in a relatively straight manner which reduces or eliminates the need to rotate the cage 10, which can reduce or minimize incorrect orientation or impingement upon important anatomical structures, such as the spinal canal, spinal nerves, abdominal vasculature. The surgeon may use the insertion tool or surgical instrument 61 (FIG. 14) inserted into the lateral slots 60 and 62 to facilitate placement and proper positioning. Note that the nose or front portion 28 of the cage 10 is adapted to facilitate insertion into the disk area 11. The cage 10 may be pivoted or rotated to a proper position as suggested in FIGS. 20A-22D. Graft material may be inserted in a conventional manner into the cage 10. Typically, the graft is placed prior to the insertion of the cage. The cage 10 is then placed using a posterolateral or transforamenal approach and rotated or pivoted if necessary. Thereafter, the patient is closed and the procedure is finished in a conventional manner.

While the method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:
1. A prosthetic implant system comprising:
a fusion cage comprising a cage body having a plurality of surfaces, said plurality of surfaces cooperating to define a multi-planar angulation adapted to achieve substan- tially flush fitment in a lordotic disk space between adjacent vertebrae when said fusion cage is inserted in said lordotic disk space; and an insertion tool for securing to said fusion cage to permit a user to insert and place said fusion cage into a disk area;

said fusion cage comprising a plurality of apertures or slots, said plurality of apertures or slots being of different shapes or sizes;

said insertion tool having a plurality of projections having a plurality of different shapes or sizes that complement the shapes or sizes of the plurality of apertures or slots, respectively, to prevent relative rotational movement between said insertion tool and said fusion cage;

wherein said insertion tool further comprises indicia to facilitate proper placement of said fusion cage after said fusion cage is mounted on the insertion tool and before it is inserted between said adjacent vertebrae;

said plurality of apertures or slots being asymmetrical for directional coupling of said fusion cage to said insertion tool.

2. The prosthetic implant system as recited in claim 1 wherein said cage body comprises a longitudinal plane along a longitudinal axis and a cross-sectional plane along a cross-sectional axis that is generally non-parallel to said longitudinal axis, said cage body being non-symmetrical about either of said longitudinal plane or said cross-sectional plane.

3. The prosthetic implant system as recited in claim 1 wherein said cage body comprises a first surface and a second surface coupling said plurality of surfaces;

said first surface defining a first surface area and said second surface defining a second surface area, wherein said first and second surface areas are different.

4. The prosthetic implant system as recited in claim 1 wherein said cage body defines a trapezoid or trapezium in a cross-sectional plane that is generally perpendicular to a longitudinal axis.

5. The prosthetic implant system as recited in claim 4 wherein said trapezoid or trapezium gets smaller along said longitudinal axis from a first end to a second end.

6. The prosthetic implant system as recited in claim 4 wherein said cage body defines a second trapezoid or trapezium in a second cross-sectional plane that is generally perpendicular to a longitudinal axis, said cross-sectional plane and said second cross-sectional plane being different in shape or area.

7. The prosthetic implant system as recited in claim 1 wherein said adjacent vertebrae comprises a first vertebra and a second vertebra, a first surface of said first vertebra cooperates with a second surface of said second vertebra to define said lordotic disk space, said cage body comprises a top defining a top surface for engaging said first surface of said first vertebra and a bottom surface for engaging said second surface of said second vertebra, wherein said cage body is adapted to cause said top and bottom surfaces of said cage body to engage said first and second surfaces substantially flush after said fusion cage is inserted into said lordotic disk space at an angled or diagonal trajectory.

8. The prosthetic implant system as recited in claim 1 wherein at least one of said plurality of apertures or slots is defined by at least one generally U-shaped wall.

9. The prosthetic implant system as recited in claim 8 wherein each of said plurality of apertures or slots is defined by at least one generally U-shaped wall.

10. The prosthetic implant system as recited in claim 1 wherein said fusion cage comprises at least one graft window that opens into an interior area of said fusion cage, at least one of said plurality of apertures or slots being in communication with said at least one graft window.

11. The prosthetic implant system as recited in claim 1 wherein said cage body is adapted such that when it is inserted substantially diagonally or angled with respect to an anterior-posterior axis, said first and second surfaces engage said first and second vertebrae substantially flush.

12. The prosthetic implant system as recited in claim 1 wherein said cage body comprises a shape that is polygonal and non-circular in any plane.

13. The prosthetic implant system as recited in claim 1 wherein said plurality of surfaces comprises a first planar surface and a generally opposed second planar surface, said cage body is symmetrical about a diagonal axis across said first planar surface.

14. The prosthetic implant system as recited in claim 1 wherein said fusion cage is symmetrical about a longitudinal horizontal plane.

15. The prosthetic implant system as recited in claim 1 wherein said fusion cage is asymmetrical about a longitudinal horizontal plane.

16. The prosthetic implant system as recited in claim 15 wherein said fusion cage is asymmetrical about a longitudinal vertical plane.

17. The prosthetic implant system as recited in claim 1 wherein said fusion cage is asymmetrical about a longitudinal vertical plane.

18. The prosthetic implant system as recited in claim 1 wherein each of said plurality of apertures or slots are defined by a wall that extends from a tool insertion end of said fusion cage toward, but not through, a generally opposing second end of said fusion cage.

19. The prosthetic implant system as recited in claim 1 wherein said plurality of apertures or slots are defined by a plurality of walls, respectively, that are non-circular.

20. The prosthetic implant system as recited in claim 1 wherein said fusion cage comprises a threaded aperture, said insertion tool comprising a threaded member for screwing into said threaded aperture to secure the fusion cage to the insertion tool.

21. The prosthetic implant system as recited in claim 20 wherein said plurality of apertures or slots being interior to side walls of said fusion cage and said insertion tool comprises a plurality of projections being male projections adapted for receiving in said plurality of apertures or slots.

22. The prosthetic implant system as recited in claim 1 wherein said plurality of surfaces cooperate to define a biplanar angulation.

23. The prosthetic implant system as recited in claim 1 wherein said cage body has a first surface generally opposed to a second surface, said first and second surfaces cooperating to define a compound angle and defining a biplanar angulation.

24. The prosthetic implant system as recited in claim 23 wherein the at least one of said first or second surfaces are arcuate or convex in cross-section.

25. The prosthetic implant system as recited in 1 wherein a first surface and a second surface converge along a longitudinal axis and in a direction generally perpendicular to said longitudinal axis, said first and second surfaces cooperating to define a compound angle.

26. The prosthetic implant system as recited in claim 25 wherein said compound angle is adapted to cause said first and second surfaces to engage said first and second vertebrae substantially flush when said fusion cage is inserted at an angled or diagonal trajectory into a disk area.

27. The prosthetic implant system as recited in claim 25 wherein said cage body comprises a longitudinal axis and a cross-sectional axis, each of said first and second surfaces cooperating to define a first angle along said longitudinal axis and a second angle along said cross-sectional axis, each of said first and second angles being an acute angle.

28. The prosthetic implant system as recited in claim 27 wherein said first and second angles are different.

29. The prosthetic implant system as recited in claim 25 wherein said adjacent vertebrae comprise a first vertebra and a second vertebra, said first and second vertebrae cooperating to define a second compound angle, said second compound angle being adapted so that said first and second surfaces engage said first and second vertebrae substantially flush when said cage body is inserted into a disk area substantially diagonally or angled with respect to an anterior-posterior axis.

30. The prosthetic implant system as recited in claim 29 wherein said compound angle and said second compound angle are different.

31. The prosthetic implant system as recited in 1 wherein a first surface lies in a first plane and a second surface lies in a second plane, said first and second planes being non-parallel in cross-section along a longitudinal axis and also being non-parallel in cross-section along an axis generally perpendicular to said longitudinal axis.

32. The prosthetic implant system as recited in claim 1 wherein said indicia comprises verbiage to indicate proper orientation of said fusion cage.

33. The prosthetic implant system as recited in claim 1 wherein said plurality of apertures or slots and said plurality of projections on said insertion tool are adapted to cause said fusion cage to assume a predetermined orientation with respect to said insertion tool.

34. The prosthetic implant system as recited in claim 33 wherein said indicia is located on a surface of at least one of said insertion tool or said fusion cage so that a surgeon can see said indicia during said insertion and placement of said fusion cage.

35. The prosthetic implant system as recited in claim 1 wherein said multi-planar angulation and said insertion tool are adapted to permit said fusion cage to be inserted and placed using a posterolateral approach.

36. The prosthetic implant system as recited in claim 1 wherein at least one of said plurality of projections is adapted to secure said insertion tool to said fusion cage and at least one other of said plurality of projections is used to orient said fusion cage with respect to said insertion tool.

* * * * *